United States Patent [19]

Salser et al.

[11] Patent Number: 4,497,796
[45] Date of Patent: * Feb. 5, 1985

[54] GENE TRANSFER IN INTACT MAMMALS

[75] Inventors: Winston A. Salser; Martin J. Cline, both of Pacific Palisades; Howard D. Stang, Van Nuys, all of Calif.

[73] Assignee: The Regents of the University of California, Berkeley, Calif.

[ * ] Notice: The portion of the term of this patent subsequent to Aug. 2, 2000 has been disclaimed.

[21] Appl. No.: 447,858

[22] Filed: Dec. 8, 1982

Related U.S. Application Data

[63] Continuation of Ser. No. 134,234, Mar. 26, 1980, Pat. No. 4,396,601.

[51] Int. Cl.$^3$ .............................................. A61K 35/12
[52] U.S. Cl. ........................................ 424/95; 424/94; 435/68; 435/172.3; 435/241; 935/62; 935/71; 935/70
[58] Field of Search ...................... 424/95, 94; 435/68, 435/172, 241

[56] References Cited

U.S. PATENT DOCUMENTS

| | | | |
|---|---|---|---|
| 4,172,124 | 10/1979 | Koprowski et al. | 435/172 |
| 4,196,265 | 4/1980 | Koprowski et al. | 435/172 |
| 4,276,282 | 6/1981 | Sugimoto et al. | 435/179 |
| 4,285,929 | 8/1981 | Sugimoto et al. | 435/172 |

Primary Examiner—Sam Rosen
Attorney, Agent, or Firm—Bertram I. Rowland

[57] ABSTRACT

Methods and compositions are provided for gene transfer to intact mammals with expression of the exogenous genetic material in the host. Mammalian host cells which are regenerative, normally highly proliferative or subject to induced proliferation, are transformed or modified in vitro with DNA capable of replication and expression in the host cell, wherein the DNA becomes incorporated into the cell. The modified cells are found to regenerate in the host with expression of the introduced DNA. Particularly, mammalian cells were modified with genes providing for overproduction of a particular enzyme. The modified cells were reintroduced in the host under conditions providing for selective advantage of the modified cells.

7 Claims, No Drawings

GENE TRANSFER IN INTACT MAMMALS

The invention described herein was made in the course of, or under, a grant from the United States Public Health Service.

CROSS-REFERENCE TO RELATED APPLICATIONS

This is a continuation application of pending patent application Ser. No. 134,234, filed Mar. 26, 1980, now U.S. Pat. No. 4,396,601.

BACKGROUND OF THE INVENTION

1. Field of the Invention

The discovery that one could introduce exogenous genes into a bacterial host in vitro and observe expression of the exogenous genes in the bacterial host opened up vistas of new capabilities for the production of a wide range of compounds, particularly proteins, improved methods of treating waste, novel types of fertilizers, and new vaccines. While transformation of prokaryotes offer many new and yet envisaged opportunities, there is also great interest in being able to modify eukaryotes and particularly mammalian cells.

Many diseases are genetically related involving genetic deficiencies, which are usually either failure to produce a gene product or production of an abnormal product. Other situations involve treatment of a host with drugs which may have substantial toxicity to host cells. In these instances, it would be desirable to provide the host with the missing capability, the normal capability or a defense mechanism against the detrimental effects of the drug. The capability to modify a host's genetic structure to provide for either additional genetic capabilities or reparation of a defective capability on a temporary or permanent basis opens up wide avenues in the treatment of genetic deficiencies and disease.

2. Description of the Prior Art

Methods of introducing genetic material into a host cell include viral vectors Munyon et al. *J. Virol.* 7:813–820, 1971; cell-cell fusion, the fusion to cells of a limited number of chromosomes enveloped in nuclear membranes, Fournier et al. *Proc. Natl. Acad. Sci.* 74:319–323, 1977; and cellular endocytosis of microprecipitates of calcium-DNA complex, Bachetti and Graham, ibid. 74:1590–1594, 1977; Maitland and McDougall, *Cell* 11:233–241, 1977; Pellicer et al. ibid. 14:133–141, 1978 and Wigler et al. ibid. 14:725–731, 1978. Cell lines lacking thymidine kinase are readily transformed by appropriate DNA to a tk+ status when grown in the presence of a folic acid inhibitor and thymidine. Pellicer, supra and Wigler, supra.

SUMMARY OF THE INVENTION

Methods and compositions are provided for providing mammalian hosts with additional genetic capability, either a novel capability or enhancement of an existing one. Host cells capable of regeneration are removed and treated with genetic material under conditions whereby the genetic material is introduced into the host cells and becomes capable of replication and expression. The introduced genetic material includes at least one marker which allows for selective advantage for the host cells in which the introduced genetic material is capable of expression. The host cells are returned to the host under regenerative conditions, preferably of rapid proliferation of the cells, optionally with stressing of the host to provide a selective advantage for the genetically modified cells. It is found under these conditions, that the modified cells proliferate and express the genetic material which was introduced. Particularly, genetic material was employed which provided for expression of an enzyme. Either under the normal conditions of the host or subjecting the host to an enzyme antagonist, a selective proliferative advantage for the modified cells having overproduction of the enzyme resulted, in contrast to the normal cells incapable of such overproduction. By use of this approach, animals were obtained in which the majority of the type of cells involved contained the added genetic material in a functionally active state.

DESCRIPTION OF THE SPECIFIC EMBODIMENTS

In accordance with the subject invention, a host is genetically modified by removing from the host or syngeneic source cells capable of regeneration when present in the host. The cells are then combined with DNA having genes capable of expression to provide a selective advantage for cells, under conditions where cells incorporate the DNA. The cells, which will include cells having the additional DNA, are then returned to the host. The genes providing the selective advantage can be combined with other genetic material which will be incorporated in conjunction with the gene supplying the selective advantage. The gene providing the selective advantage will be referred to as the selective marker.

Various methods may be employed for introduction of the genetic material, each of the methods having advantages and disadvantages. After introduction of the treated cells into the host, conditions are maintained in the host naturally, by administration of a physiologically active compound, or by dietary exclusion, to provide a selective advantage for the cells which have been genetically modified. In this way, genetic functions can be provided for a variety of purposes including treatment of genetic deficiencies, which includes providing a genetic capability which the host lacks or production of a normal product where the host produces an abnormal one; production of enzymes which can protect the host from cytotoxic agents; or for production of a wide variety of proteins e.g. hormones, globulins or the like.

In describing the invention, the host and host cells will be considered first, followed by the genetic material which may be employed for modifying the host cells and the manner in which the host cells are modified, and concluding with the regeneration of the modified cells and the purposes and effect of expression of the genetic material introduced into the modified cells.

HOST AND HOST CELLS

Various mammalian hosts may be treated in accordance with the subject invention, such as homo sapiens and domestic animals, particularly bovine, equine, ovine and procine. The type of host cell which will be employed is one which is capable of regeneration, preferably rapid proliferation, either naturally or induced; can be isolated from the host or syngeneic source; can be modified by introduction of genetic material, which genetic material will then be capable of expression and replication; can be maintained in vitro, so as to be returned to the host in a viable state; are capable of being returned to the source in the host; and can provide the added genetic function in a form which is useful to the host.

Among potential cells which may be employed are bone marrow cells, particularly stem cells which provide hematopoietic functions. Other examples of tissues which have persistent stem cells include the intestinal mucosa and the germ line tissues. Use of these techniques to introduce genes into germ line cells may be of especial interest in breeding improved strains of domestic animals. Other cells which can be employed include cells of regenerative organs e.g. liver. Any body member which is regenerative or can be induced to regenerate can be a source of cells.

Bone marrow cells chosen for modification should optimally be populations rich in stem cells. Furthermore, the cells chosen are preferably dividing, rather than stationary cells. To increase the fraction of these types of cells, the host may be treated by various techniques to increase the level of proliferating cells. For example, vinca alkaloids may be employed which inhibit mitosis, followed by radid proliferation of the cells.

A wide variety of genetic material (DNA) may be employed to provide for the selective marker. The selective marker will allow for rapid proliferation of the modified cells in the host under normal conditions of the host or where rapid proliferation is subject to inhibition. The inhibition can be as a result of introduction of a drug which inhibits (a) proliferation because of interference with transcription of DNA or translation of RNA, that is, expression of one or more genes; (b) cell membrane formation; (c) cell wall formation; (d) enzyme activity; or (e) combinations thereof.

A wide variety of drugs are known which are employed for the treatment of disease which inhibit cell replication, so as to favor the host against a parasitic invader such as bacteria, protozoa, or even a neoplastic variant of the host cell. The effectiveness of the drug may be inhibited in a cell by introducing into the cell genes which express an enzyme which reacts with the drug to deactivate it, genes which overproduce an enzyme involved in the metabolic pathway which the drug inhibits, so as to provide a selective advantage for the cells having higher concentrations of the enzyme(s), or genes which would provide for a metabolic pathway less affected by the drug, than the endogenous metabolic pathway.

Alternatively, the enzyme can provide for increased production of a metabolite essential to mitosis e.g. a metabolite on the biosynthetic pathway to DNA or RNA, for example, the formation of nucleosides. The modified cells having the selective marker which provides for enhanced enzyme production permits the modified cells to compete more effectively for a limited amount of metabolite precursor against the wild type cell.

The genetic material which is employed for recombination with the host cells may be either naturally occurring, synthetic, or combinations thereof. Depending upon the mode employed for introduction, the size of the genetic material introduced will vary. Furthermore, when two or more genes are to be introduced they may be carried on a single chain, a plurality of chains, or combinations thereof. Restrictions as to the size of a DNA fragment will be as a result of limitations due to the technical aspects of the vector: if a recombinant DNA is to be used, by the packaging requirements of a viral vector; the probability of transfer into the recipient cells by the method employed; the manner of preparation and isolation of the DNA fragments; or the like.

The selective markers employed can be chosen to deactivate an antimetabolite to mammalian cells, by reacting with the antimetabolite and modifying the antimetabolite to an ineffective product. Various enzymes and their genes are known and have been isolated for deactivating drugs. The most numerous examples are bacterial enzymes which deactivate antibiotics, such as those enzymes which confer resistance to aminoglycosides and polymyxines (streptomycin, kanamycin, neomycin, amikacin, gentamicin, tobramycin, etc.), and the like. Another drug which may find use is PALA. Where the drug does not provide a selective advantage, since the host metabolic pathways are not involved, a gene providing resistance to such a drug would not be useful. Illustrative of this situation are sulfonamides, which block a bacterial pathway, but not a mammalian metabolic pathway.

Alternatively, rather than providing a gene which expresses an enzyme, one could provide a gene which is not subject to interference by the drug. For example, one could employ DNA having a mutation at the site at which the drug binds or DNA which results in RNA or a protein, which substantially reduces the binding of the drug to the site at which the drug is active. Illustrative of drugs which are active by binding to specific sites are the macrolides, e.g. erythromycin and aminoglycosides, e.g. streptomycin.

The next group of drugs are chemotherapeutic agents. Protection of the host cells from the chemotherapeutic agents may be provided by introducing genes which overproduce the enzyme inhibited by the drug or deactivate the drug. Illustrative drugs include methotrexate, which inhibits dihydrofolate reductase, purine analogs, which interfere with the enzymes involved with inosinic acid, and pyrimidine analogs, such as fluorouracil, which inhibits thymidine monophosphate synthesis.

The selective marker may provide for enhanced production of one or more metabolites involved in proliferation, for example, production of nucleotides or nucleosides. An illustrative gene is the gene which codes for thymidine kinase, which is involved in the biosynthetic pathway to thymidylic acid. This selective advantage need not be associated with antimetabolite administration to the host.

In some genetic diseases the gene which corrects the genetic defect may itself confer a replicative advantage. For example, the insertion of genes for adenosine deaminase into cells of the marrow of certain patients with combined immunodeficiency disease may confer a selective advantage upon the replication of their stem cells leading to the production of a large population of immunocompetent cells which will ameliorate the effects of the disease.

Finally, one may employ genes which provide for production of a protein other than an enzyme, which allows for selective advantage of the modified cells. For example, this can be as a result of production of inducer which prevents repression of translation to provide semiconstitutive or constitutive production of an enzyme. In such cases a regulator gene may confer selective advantage even when no drug is employed.

In summation, the types of DNA which will be employed for selective markers include genes which react with drugs which interfere with regeneration so as to destroy activity of the drug; genes which provide sites which are not susceptible to drug action, so as to prevent the drug's action in the particular cell; genes which are repetitive for production of a desired protein e.g. an enzyme, which is inhibited by the drug; or genes which affect the regulatory function of the cell, so as to provide for overproduction of a particular enzyme by the natural processes of the cell, and which increase the normal replication of the cell genes to enable the cell to better compete for limited resources within the body.

If a drug is to be employed for providing the selective advantage the gene employed must be appropriately related to the drug. The particular drugs employed must be considered as to level of toxicity and effect on the particular tissue which is being modified. Also to be considered is the purpose of the modification, which may limit the involved drug. In other cases the appropriate selective marker may be related to correction of the genetic deficiency involved with the disease or may alter the cells proliferation in any of various ways.

A number of ways have been developed for insertion of genetic materials into cells. Included among these techniques are viral vectors, Munyon et al., supra; cell-cell fusion involving the fusion to cells of a limited number of chromosomes enveloped in nuclear membranes, Fournier and Ruddle, supra; cellular endocytosis of microprecipitates of calcium-DNA complex, Bachetti and Graham, supra, Maitland and McDougall, supra, Pellicer et al., supra and Wigler et al., supra: minicell fusion; fusion with liposomes containing DNA; fusion with bacterial protoplasts containing plasmid DNA; and fusion with erythrocyte ghosts packaged with DNA. Each of the techniques has advantages and disadvantages, such as efficiency of information insertion, selectivity as to the particular nature or information of the DNA, permissible size of the DNA fragment, and the like.

When employing the microprecipitates of calcium-DNA complex, the DNA employed may provide for a single gene, a single set of genes, e.g. the beta-globin gene cluster, or a plurality of unrelated genes. As previously indicated, the size of the DNA fragments will vary, depending upon the particular manner used to introduce the genetic information. The mixtures of DNA which are not covalently linked may be introduced by congression, that is, different fragments of DNA will frequently concurrently enter a suspectible cell, so that those cells which have the selective marker are also likely to have the genetic capability of the additional genes.

The presence of a selective marker allows for selective pressure for preferential regeneration of the modified cell. Thus, in situations where gene deficiencies exist which would not provide for selective advantage of a modified cell, the selective marker affords this capability. With bone marrow cells, the cells could be modified by introducing genes which would provide for the correction of genetic deficiencies, by expression of products in which the host is deficient or provide for a wild type gene for correct expression of a protein. With bone marrow stem cells, genes could be provided with the correct sequence to correct hemoglobinopathies, such as sickle cell disease and thalassemia. Other defects could include defects in the production of plasma coagulation factors, e.g. fibrinogen, prothrombin and the various Factors, especially Factors VIII and IX. By introducing genes providing for structurally normal proteins fulfilling these functions, in conjunction with the ability to provide selective pressures for the modified cells, the modified cells may be maintained in the host of a high level for extended periods of time.

Depending upon the nature of the cells, the cells may be introduced into the host in various ways. With bone marrow or liver cells, the cells may be introduced intravenously. It may be desirable to treat the host to reduce the relevant cell population so that rapid cell replication will be favored. Various techniques can be employed to achieve this result, such as the use of mitotic inhibitors, e.g. vinca alkaloids, irradiation with X-rays, or other technique. It is desirable that prior to the introduction of the modified cells to the host, the host have a low level of the relevant cell type so that after introduction, there may be a rapid and expanding proliferation of the modified cells.

After introduction of the modified cells into the host, the host will be stressed with relevent drug(s) if these are to be employed to provide selective pressure for the modified cells. Appropriate levels of the drug may be maintained to insure proliferation of the desired cells. Depending upon the drug, the nature of the cells, and the concerns with repetitive introduction of modified host cells, the drug treatment may be of relatively short or long term duration. It is found that even after termination of the treatment with the drug providing the selective pressure, the cells continue to proliferate and may be maintained at a high level for extended periods of time.

The following examples are offered by way of illustration and not by way of limitation.

EXPERIMENTAL

The following is a flow chart of the progress of the experimentation:

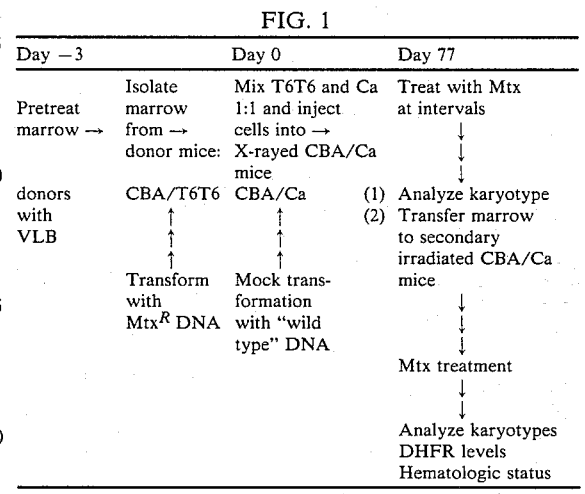

FIG. 1

Transformation of Mouse Bone Marrow In Vitro

Mouse fibroblast Swiss 3T6 cells highly resistant to Mtx and containing reiterated structural genes specifying DHFR were employed (See Kellems et al. J. Biol. Chem. 254:309–318., 1979). They were maintained in $4 \times 10^{-4}M$ methotrexate (Mtx) and designated 3T6 R1. DNA was isolated from 3T6 R1 and from non-resistant (wild type) mouse cell lines including 3T6 (fibroblastic) and L1210 (lymphocyctic leukemia) and in later experiments from salmon sperm (Sigma). The relative ratio of dihydrofolate reductase synthesis and number of gene copies in 3T6 R1 and 3T6 was approximately 30 to 1. DNA coprecipitated with calcium phosphate was used to transform wild type L1210 cells to methotrexate resistance by the method of Bachetti and Graman, supra, as modified by Wigler et al. supra.

Equal numbers of CBA/Ca and CBA/H-T6T6 mice were injected intraperitoneally with 3 or 4 mg/kg of the mitotic inhibitor vinblastine 3 days before marrow was removed for in vitro transformation. Mitotic inhibition by this treatment is followed by a burst of proliferation. Assays of colony-forming cells (CFU-S), when compared with total cell counts, showed that suspensions from animals thus treated were relatively depleted of mature cells and enriched approximately 3-fold in pluripotent spleen colony-forming cells (CFU-S). On the day of transformation (designated day 0, FIG. 1) single cell suspensions in McCoy's 5A medium with 15% fetal calf serum were obtained from femurs and tibias of sacrificed animals.

Cells from Ca and T6T6 animals were placed in separate pools. All T6T6 animals had the characteristic marker chromosome abnormality. Cell suspensions of $5 \times 10^6$ in 10 ml complete medium were incubated with 1.0 ml Ca-precipitated DNA containing a total of 40 μg DNA as described by Wigler et al., supra, for 4 hours at 37° C. in 5% $CO_2$ in tissue culture flasks. For cells to be transformed to Mtx resistance, either 2 or 4 μg of DNA was from the 3T6R1 cell line. During this period differentiated phagocytic marrow cells firmly adhered to the flask.

T6T6 cells were incubated with DNA from 3T6 R1 Mtx-resistant cells, and CBA/Ca marrow cells were incubated with control DNA preparations from Mtx-sensitive cells. Thereafter, loosely adherent cells were collected and centrifuged at $150 \times g$ for 10 min and resuspended in DNA-free complete medium. After careful cell counts, Ca and T6T6 cells were combined in a ratio of 1:1 and between $5 \times 10^6$ and $5 \times 10^7$ of the combined cells were injected intravenously into recipient CBA/Ca mice in a volume of 0.3 to 0.4 ml in McCoy's medium with fetal calf serum. These recipients had received 850 rads irradiation from the cobalt source 24 hours previously to eradicate endogenous hematopoiesis. This dose or irradiation was selected because it had low lethality but virtually eradicated endogenous spleen colony-forming cells (CFU-S). Thus an average of $2 \pm 1$ endogenous CFU-S after 850 rads and $0.5 \pm 0.5$ endogenous CFU-S after 900 rad whole body irradiation was observed in this mouse strain. Between 48 and 96 hours after injection, the recipient animals began treatment with the previously established Mtx protocol.

Hematopoietic Effects of Methotrexate Treatment in the Mouse

An appropriate schedule of Mtx treatment which would select for drug-resistant hematopoietic cells without lethality in control animals was established as follows. Groups of normal CBA or C3H mice weighing between 18 and 25 g were treated by a thrice weekly schedule of intraperitoneal injections of Mtx in doses varying between 0.5 and 8 mg/kg per injection. An escalating schedule of 0.5 mg/kg for 4 doses, 2 mg/kg for 4 doses and then 4 mg/kg thrice weekly was selected as not lethal but having profound suppressive effects on hematopoiesis. Tibial cellularity, peripheral white cell counts and hematocrits were all depressed in Mtx-treated animals and megaloblastic morphologic changes developed in the bone marrows. The hematocrit and tibial cellularity were found to be the easiest and most reliable hematologic parameter to follow and remained depressed in animals continuously treated with Mtx for at least 3 months. False elevations of hematocrit in Mtx-treated mice were occasionally observed in sick and dehydrated animals. No difference in sensitivity to Mtx was observed in the mouse strains CBA/Ca and CBA/H T6T6 as measured by standard hematologic parameters over 3 months of observation.

Selection of Drug Resistance Marrow Cells

The irradiated mice receiving mixtures of control Ca cells and T6T6 cells transformed with 3T6 R1 DNA were treated with Mtx for periods of 24 to 77 days. At intervals, animals were sacrificed or subjected to a limb amputation to obtain bone marrow samples. These were analyzed for karyotype distribution, cellularity, CFU-S content and injected into secondary irradiated CBA/Ca recipients. The results of two initial experiments are shown in Tables I and II.

TABLE I

EXPERIMENT MB2. KARYOTYPE ANALYSIS OF MARROW CELLS OF IRRADIATED CBA/Ca MICE RECEIVING A 1:1 MIXTURE OF CONTROL Ca and TRANSFORMED T6T6 MARROW CELLS

| Recipient* | Duration of Mtx Treatment (days) | Karyotype (% T6T6) |
|---|---|---|
| Primary 1 | 0–24 | 57 |
| Primary 2 | 0–32 | 59 |
| Secondary 2 | 32–46 | 79 |
| Primary 3 | 0–39 | 67 |
| Secondary 3a | 39–53 | 97 |
| Secondary 3b | 39–67 | 93 |
| Secondary 3c | 39–73 | 84 |

*Irradiated CBA/Ca recipients of the 1:1 mixture of a Ca transformed with wild type DNA and T6T6 cells transformed with 3T6R DNA are designated "primary" and each mouse is given a unique number. The day of infusion is designated "0." Recipients of marrow from "primary" animals are designated "secondary" and bear the same identifying number. Karyotype analysis of recipient bone marrow cells were performed after the designated interval of methotrexate treatment. Between 50 and 100 chromosome spreads were analyzed.

TABLE II

EXPERIMENT TV4. KARYOTYPE ANALYSIS OF MARROW CELLS OF CBA/Ca MICE RECEIVING A 1:1 MIXTURE OF CONTROL Ca and TRANSFORMED T6 MARROW CELLS

| Recipient* | Days with Mtx | Days Without Mtx | Karyotype (% T6) |
|---|---|---|---|
| Primary 1 | 0–33 | — | 79 |
| Primary 2 | 0–40 | — | 75 |
| Primary 3 | 0–47 | — | 74 |
| Primary 3 | 0–47 | 48–68 | 83 |
| Secondary 3 | 47–61 | — | 88, 88, 100* |
| Primary 4 | 0–54 | — | 75 |
| Secondary 4 | 54–72 | — | 83 |
| Primary 5 | 0–65 | — | 96 |
| Primary 5 | 0–65 | 66–113 | 63 |

*Irradiated recipients of the 1:1 mixture of Ca cells transformed with wild type DNA and T6T6 cells transformed with 3T6R1 DNA are designated "primary" and each mouse is given a unique number. The day of infusion is designated "0." Recipients of marrow from "primary" animals are designated "secondary" and bear the same identifying number.
**Three secondary recipients. Between roughly days 30 and 40 a clear increase in the percentage of bone marrow cells displaying the T6T6 marker was observed in primary recipient animals. Marrow from these mice was injected into irradiated secondary recipients which were then treated with methotrexate. They, too, showed an increased ratio of T6T6 to Ca karyotypes, above that seen in the primary marrow recipients. Seven such experiments were performed and this same pattern was seen in five independent experiments involving 19 primary recipient animals and 30 secondary recipients. Only two experiments during this same period failed to show a predominance of transformed karyotype.

When methotrexate treatment of animals receiving transformed marrow cells was stopped, the predominance of T6T6 karyotypes persisted for at least 3 weeks (Primary Recipient 3, Table III) but gradually diminished by 8 weeks without treatment (Primary Recipient 5, Table II).

TABLE III

KARYOTYPE ANALYSIS OF BONE MARROW AND PLURIPOTENT STEM CELLS FROM CBA/Ca MICE RECEIVING 1:1 MIXTURE OF CONTROL Ca AND TRANSFORMED T6T6 BONE MARROW CELLS

| Recipient | Duration of Mtx (days) | Bone Marrow Karyotype T6T6 (%) | Karyotype of Spleen Colonies T6T6 (%) | Ca (%) | Mixed (%) |
|---|---|---|---|---|---|
| Primary 1 | 0–24 | 57 | 50 | 50 | 0 |
| Primary 2 | 0–40 | 75 | 57 | 26 | 17 |
| Primary 3 | 0–47 | 74 | 58 | 8 | 33 |

Individual spleen colonies were removed 10 days after innoculation of irradiated recipient with bone marrow cells. A single cell suspension was made from each colony and cells were incubated with colcemide 3 μg/ml for 90 minutes before treatment with hypotonic KCL and fixation with acetic acid/ethanol for chromosome spreads.

In order to analyze whether the predominance of T6T6-marked cells involved pluripotent stem cells as well as other proliferating marrow cells, marrow was taken from selected primary recipient animals and $5 \times 10^4$ cells were injected into irradiated recipient CBA/Ca mice in a typical spleen colony-forming (CFU-S) assay. (Tell and McCulloch Rad. Res. 14:213, 1961) Ten days later the secondary recipients were killed and individual spleen colonies removed for karyotype analysis. As seen in Table III the percentage of T6T6 karyotype predominated in the pluripotent marrow stem cell population. Mixed T6T6-Ca spleen colonies were also seen, presumably resulting from development of T6T6 colonies on a background of endogenous hematopoiesis in the Ca animals.

Effect of Drug Administration on Cell Predominance

In order to assess the significance of these results, control experiments were performed to determine whether T6T6-marked cells had any proliferative advantage or increased resistance to Mtx and to analyze the contribution of endogenous hematopoietic repopulation in irradiated CBA/Ca animals. Experimental animals receiving an equal mixture of mock transformed Ca and mock transformed T6T6 and either untreated or treated with Mtx for up to two months had a predominance of Ca karyotypes as anticipated from the contributions of infused Ca cells and endogenous Ca cells.

TABLE IV

KARYOTYPE ANALYSIS OF MARROW CELLS OF CONTROL Ca MICE RECEIVING A 1:1 MIXTURE OF MOCK TRANSFORMED Ca AND MOCK TRANSFORMED T6T6 MARROW CELLS

| Recipient* | Duration of Mtx Treatment (days) | Karyotype (% T6T6) |
|---|---|---|
| Primary 1 | 0–33 | 31 |
| Primary 2 | 0–40 | 24 |
| Primary 3 | none | 26 |
| Primary 4 | 0–60 | 40 |
| Primary 5 | none | 21 |
| Primary 6 | 0–26 | 50 |
| Secondary 6 | 27–48 | 28 |
| Primary 7 | 0–53 | 56 |
| Primary 8 | 0–56 | 57 |
| Primary 9 | 0–42 | 40 |
| Primary 10 | 0–56 | 24 |

In primary Ca recipients of equal mixtures of mock transformed T6 and Ca cells the percentage of dividing marrow cells with the T6 marker varied between 21 and 57%. It is presumed that animals with lower percentages of T6 had restored their hematopoiesis at least in part from endogenous Ca cells surviving the irradiation.

In a final study to demonstrate transformation to drug resistance, in two independent experiments the usual procedure was reversed and Ca cells were transformed and T6 cells were used as the controls. After injection of a 1:1 mixture of Ca and T6 into irradiated T6 animals they were treated with Mtx or left untreated for two months.

TABLE V

EXPERIMENT MB6. KARYOTYPE ANALYSIS OF MARROW CELLS CBA/T6T6 MICE RECEIVING A 1:1 MIXTURE OF CONTROL T6 CELLS AND TRANSFORMED Ca MARROW CELLS

| Recipient | Exp | Mtx Treatment | Duration (days) | Karyotype (% Ca) |
|---|---|---|---|---|
| Primary 1 | 1 | Yes | 42 | 55 |
| Primary 2 | 1 | None | 59 | 33 |
| Primary 3 | 1 | Yes | 59 | 62 |
| Primary 4 | 1 | Yes | 71 | 68 |
| Primary 5 | 1 | None | 71 | 35 |
| Primary 6 | 1 | Yes | 97 | 72 |
| Primary 1 | 2 | Yes | 56 | 67 |
| Primary 2 | 2 | None | 56 | 40 |

Recipient T6 mice received aliquots of a 1:1 mixture of T6 cells transformed with wild type DNA and Ca cells transformed with 3T6 R1 DNA. Animals were either untreated or treated with Mtx.

As shown in Table V, the Ca karyotype predominated only when Mtx was administered. This gave an unambiguous demonstration that drug therapy determined the predominant marrow population and that the karyotype per se did not influence predominance; i.e., there was no inherently greater resistance to Mtx associated with either the CBA/Ca strain or the CBA/HT6T6.

Hematologic Status of Mice Receiving Transformed Marrow

After it was demonstrated that cells transformed with Mtx-resistant DNA predominated in the marrows of drug-treated recipient animals, simple tests were performed to assess the animals' hematologic status.

TABLE VI

HEMATOLOGIC STATUS OF MICE RECEIVING TRANSFORMED BONE MARROW*

| Recipients | Mtx treatment (days) | CFU-S (per 5 × $10^4$ cells) | Tibial Cellularity | Hematocrit (%) |
|---|---|---|---|---|
| Controls: saline-treated (15) | none | 11.3 (5–15) | 8.7 (7.1–10.6) | 42 (38–47) |
| Controls: Mtx-treated (15) | 21–77 | — | 3.9 (3.3–4.9) | 26 (23–39) |
| Primary 1 | 0–33 | 8.8 (7–9) | 13.9 | — |
| Primary 2 | 0–40 | 16 (13–19) | 9.6 | — |
| Primary 3 | 0–47 | 22 (18–25) | 6.0 | — |
| Primary 4 | 0–54 | — | 9.6 | — |
| Secondary 4 | 54–72 | — | 6.6 | 40 |
| Primary 5 | 0–65 | — | 8.2 | 47 |

*Control animals received no irradiation or bone marrow cells and were injected with saline or Mtx as described. Number of animals is indicated in parentheses in column one. Numbers in parentheses in other columns indicate the range of values observed. Primary recipient CBA/Ca mice were irradiated (850 rads) and received a 1:1 mix of control Ca and transformed T6 cells before treatment with Mtx for the periods indicated. Secondary recipients were irradiated and received marrow from primary recipients. CFU-S were assayed by injecting 5 × $10^4$ marrow cells into irradiated CBA/Ca recipient mice and counting spleen colonies 10 days later. (Tall and McInttosh, supra)

The results displayed in Table VI indicate that animals receiving transformed bone marrow and methotrexate have high hematocrits and tibial cellularity relative to control animals receiving methotrexate but no transforming DNA. Further, they have high levels of CFU-S similar to control animals which received neither radiation nor bone marrow cells. Similar results were seen in other independent experiments. Thus, the hematologic status of mice receiving transformed bone marrow treated with 3T6 R1 DNA in vitro returned toward normal despite persistent treatment with methotrexate. Autopsies were performed on these animals at intervals up to 150 days after transformation and sections of visceral organs were taken for microscopic review. These studies revealed no abnormalities and the animals were clinically well at the time of sacrifice.

DHFR (Dihydrofolate Reductase) Assay

To assess whether drug resistance was related to higher enzyme levels in mice receiving transformed bone marrow, spleens were removed from primary, secondary or tertiary recipients of transformed marrow from four independent experiments and assayed for DHFR. These recipient mice were initially treated with Mtx and treatment was terminated 5-7 days prior to the collection of tissue for the DHFR assays. Appropriate controls from 12 syngeneic animals either irradiated or not, and untreated or treated with Mtx for periods up to six weeks, were also used as spleen donors. In each case, conditions for control animals were chosen to match those of the experimental group. A radiometric assay for DHFR was performed on sonicated cell-free extracts of spleen. (See Hillcoat et al., Proc. Natl. Acad. Sci. (USA) 58:1632, 1967; Hayman et al. Anal. Biochem. 87:460, 1978).

TABLE VII

DIHYDROFOLATE REDUCTASE ACTIVITY IN SPLEEN AND KARYOTYPE ANALYSIS OF BONE MARROW IN CBA/Ca RECIPIENTS RECEIVING 1:1 MIXTURE OF CONTROL Ca AND TRANSFORMED T6T6 BONE MARROW CELLS*

| Recipient | Duration of Mtx (days) | Bone Marrow Karyotype Predominance (%) | Spec. activity (% Control) |
|---|---|---|---|
| Primary | 0–42 | 49 | 168 |
| Primary | 0–59 | 62** | 375 |
| Secondary | 39–67 | 93 | 391 |
| Secondary | 54–72 | 83 | 183 |
| Secondary | 65–107 | — | 208 |
| Tertiary | 58–80 | — | 224 |

*Spleen fragments were sonicated for 30 seconds in the cold and assayed for DHFR by the method of Hayman et al Anal. Biochem. 37:460,1978. Results are expressed as the precent of DHFR in spleens of simultaneously sacrificed control mics.
**This animal received transformed Ca cells and had Ca karyotype predominance. All others received transformed T6T6 cells.

DHFR-specific activity was approximately 2- to 4-fold greater in the spleen extracts of animals receiving transformed bone marrow than in controls. These were considered to be underestimates of the elevations of DHFR in the hematopoietic cells of animals receiving transformed marrow, since the extracts of spleen also included stromal and capsular tissues and non-proliferating lymphoid cells.

Transformation of tk+ and tk− L Cells in Vitro

The technique of Wigler et al., supra, was employed to insert herpes virus tk gene in tissue culture cells. A Bam H1 fragment containing HSVtk gene was purified by gel electrophoresis and phenol extraction from Sea-Plaque ® agarose gel. Concatemers of the fragment were constructed using T4 ligase. Mouse L cells lacking thymidine kinase (tk−) were incubated with a calcium phosphate precipitate of high concentrations of DNA containing the herpes tk gene in the plasmid vector pBR 322. After a brief period of incubation, cells were transferred to a selected medium favoring the growth of tk+ cells. Tk− cells transformed to tk+ status were selected in HAT medium which favors the growth of tk+ cells. The principle underlying these experiments is that tk+ cells can rescue themselves from the block in thymidine synthesis imposed by aminopterin in HAT medium by utilizing exogenous thymidine, whereas tk− cells lacking the kinase cannot. Tk+ clones will grow under these selective conditions. The anticipated results were observed.

TABLE VIII

THYMIDINE KINASE SPECIFIC ACTIVITY OF MOUSE CELLS TRANSFORMED IN VITRO WITH HERPES SIMPLEX VIRUS TK DNA*

| Clone | Cell Lineage | Transformation with | Specific Activity (cpm/$\mu$g) |
|---|---|---|---|
| — | Ltk− | — | 0.08 |
| — | Ltk+ (wild type) | — | 4.9–5.5 |
| 207 | Ltk− | HSVtk in plasma | 9.1 |
| 202 205 | Ltk+ | HSVtk in plasmid (3) | 10.3 |
| 214 | Ltk+ | HSVtk in plasmid (3) Sal cut and ligated (3) | 12.3 |
| 214-3 | Ltk+ | | 22. |

*Clones were derived from the parent cell line by transformation with calcium precipitated HSV plasmid DNA. Clones of Ltk− lineage were selected for and grown in HAT medium.
Cells of NCTC (wild type) lineage were selected for in medium containing $10^{-4}$ M MTX, 0.1 M thymidine and grown up in HAT medium.

Surprisingly, thymidine kinase activity of different clones varied over a considerable range, suggesting multiple expressed copies of tk gene in some transformants.

In addition to transforming tk− cells to tk+ status, wild type tk+ cells were transformed in such a manner that they contained additional copies of the tk gene of viral origin. Wild type tk+ cells will grow in HAT medium by utilizing the available thymidine and HAT medium could not be used to distinguish wild type cells from those incorporating additional copies of viral genes. Consequently, a range of methotrexate and thymidine concentrations were explored which would inhibit normal cells with a single copy of tk gene but allow cells with increased concentrations of tk to grow. These selective conditions required higher folate antagonist concentrations (methotrexate $10^{-4}$M) and lower thymidine levels (0.1 $\mu$g/ml) than used in conventional HAT medium.

Wild type (tk+) L cells were exposed to herpes virus tk DNA under transforming conditions and then cultured under selective conditions. A number of transformed clones were isolated, and some were grown to sufficient density to allow for measurement of tk-specific activity (Table VIII) and for analysis of tk-specific gene sequences in DNA by Southern hybridization. For convenience, those wild type tk+ cells transformed with herpes tk gene and containing at least one viral gene in addition to the mammalian tk gene will be designated as tk++.

Selection of tk Transformed Cells In Mice

The strategy for selection of cells transformed to tk++ was similar to that employed for selection of expression of the DHFR gene and is illustrated in FIG. 2.

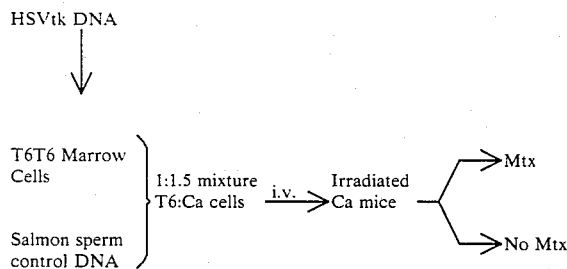

Experimental design for selecting in vivo cells transformed to Mtx resistance by calcium-precipitated HSVtk DNA. Donor T6T6 and Ca mice were pretreated with 3 mg vinblastine 3 days prior to in vitro transformation with DNA from HSVtk and salmon sperm respectively. Transformed T6 and Ca cells in a mixture of 1 to 1.5 were injected into irradiated Ca recipients, some of which were subsequently treated with Mtx, karyotype analysis of marrows from recipients was done to show predominance of T6T6 cells induced to Mtx resistance.

Mouse bone marrow cells with a distinctive chromosomal marker (T6T6) were obtained from intact normal animals and treated in vitro with a calcium microprecipitate of herpes virus tk gene. The treated marrow, presumed to contain a few stem cells transformed by viral gene, was mixed in a ratio of 1:1.5 with "mock" transformed syngeneic marrow cells lacking the chromosomal marker (CBA/Ca cells). These Ca cells had been incubated under transforming conditions with control DNA from salmon sperm. The cell mixture was injected into genetically compatible CBA/Ca animals that had been irradiated in order to greatly reduce endogenous hematopoiesis. The infused cells gradually restored blood cell formation in marrow-depleted recipients. During the period of reconstitution some of the animals were treated with methotrexate to allow for the selective proliferative advantage for those transformed cells that had incorporated one or more copies of a functional viral tk gene. Transformed cells were identified by their distinctive chromosomal marker. If there were no selective advantage to transformed cells, then the ratio of marked to unmarked dividing hematopoietic cells would be less than 1:1.5; if, however, there were a proliferative advantage, then marked cells with increased levels of tk would be found to constitute more than 50% of the dividing marrow population.

In addition to this indirect means of detecting a population of hematopoietic cells transformed to methotrexate resistance, DNA extracted from the spleens of transformed and control mice was also analyzed for the presence of sequences unique to the viral tk gene.

Simultaneous control studies were performed in which some recipients of the mixture of transformed T6 and mock transformed Ca cells were left untreated by methotrexate in order to assess the contribution of selective pressure by drug. In other control studies, equal numbers of untransformed T6 and Ca cells were injected into Ca recipients, some of whom were treated with methotrexate and others were left untreated. In further control studies, Ca marrow cells were transformed with herpes virus tk and mixed with mock transformed T6 cells. These mixtures were then injected into irradiated CBA/T6T6 animals which were subsequently examined for the predominance of Ca karyotypes in proliferating bone marrow.

The T6 marker was selected because of its ready identification and the availability of syngeneic animals possessing and lacking this marker. CBA/H-T6T6 mice have the chromosomal anomaly, whereas compatible CBA/Ca mice lack the marker. Bone marrow was selected for transformation because of its accessibility, high rate of proliferation, and the persistence of pluripotent stem cells throughout adult life. Of all the cell types present in the marrow, only transformation of appropriate stem cells should lead to the establishment of long-term hematopoietic activity in which cells bearing viral DNA sequences persisit.

The technique of transformation was as follows. Equal numbers of CBA/Ca and CBA/T6T6 mice were injected intraperitoneally with 3 mg/kg of the mitotic inhibitor, vinblastine, three days before isolating cells for transformation. Mitotic inhibition by this treatment is followed by a burst of stem cell proliferation. Marrow cells from vinblastine-treated animals were relatively depleted of mature cells and enriched approximately threefold in pluripotent spleen-colony-forming cells (CFU-S) (Smith et al., J. Nath. Cancer Inst. 40: 847–854, 1968; Till and McCulloch, Rad. Res. 14: 213, 1961) On the day of transformation, single-cell suspensions in McCoy's 5A medium with 15% fetal calf serum were obtained from femurs and tibias of sacrificed animals. Cells from Ca and T6 animals were placed in separate pools. Cell suspensions at $5 \times 10^7$ in 10 ml of complete medium were incubated with 1 ml calcium-precipitated DNA containing 8 μg herpes virus tk in plasmid form as well as purified HSVtk Bam H1 fragment (without plasmid) ligated to form concatemers. Incubation was continued for 4 hours at 37° C. in 5% $CO_2$. During this period some marrow cells adhered to the flask. A similar procedure was used for Ca cells which were incubated with salmon sperm DNA. Loosely adherent cells were collected after incubation and centrifuged at $150 \times g$ for 10 minutes, then resuspended in DNA-free complete medium. After careful cell counts, T6 and Ca cells were combined in a ratio of 1:1.5 and between $2 \times 10^6$ and $1 \times 10^7$ cells were injected intravenously into recipient CBA/Ca mice that had been irradiated 24 hours previously with 850 rads. This dose of irradiation virtually eliminated endogenous spleen colony formation. Between 72 and 96 hours after injection, the recipient animals began treatment with a previously established methotrexate protocol. An escalating schedule of 0.5 mg/kg thrice weekly for four doses, 2 mg/kg for four doses, and then 4 mg/kg thrice weekly was selected as nonlethal but having profound suppressive effects on hematopoiesis. Tibial cellularity, peripheral white counts, and hematocrits were all depressed in methotrexate-treated animals. The mice receiving mixtures of control Ca cells and transformed T6 cells were treated with methotrexate for a period of 28 to 70 days. At intervals, animals were sacrificed or subjected to a limb amputation to obtain marrow samples, which were analyzed for karyotype distribution and cellularity and injected into secondary recipient animals.

The results of one such experiment are shown in Table IX. By day 32 after transformation, a clear predominance of T6-marked cells in a dividing marrow population of a methotrexate-treated animal was observed. Control animals receiving an equal mixture of untransformed T6 and Ca cells (1:1) had a predominance of Ca karyotype. In these control recipients a ratio of Ca to T6 karyotype of greater than 1 was anticipated because of the contribution of endogenous CBA/Ca hematopoiesis in these recipient animals. In 20 such control animals none showed a predominance of the T6 karyotype.

TABLE IX
KARYOTYPE ANALYSIS OF MARROW CELLS FROM CBA/Ca MICE RECEIVING A 1:1.5 MIXTURE OF tk TRANSFORMED T6T6 AND CONTROL Ca CELLS

| Recipient | Duration of Mtx Treatment (days) | Karyotype (% T6 Cells) | Detectable viral tk DNA sequences |
|---|---|---|---|
| Primary 1 | 0–32 | 74 | Positive |
| Primary 2 | 0–47 | 84 | N.T. |
| Primary 3 | No Mtx** | 35 | N.T. |
| Primary 4 | 47–60 | N.T. | Positive |
| Secondary 4 | 60–89 | 17 | Negative |
| Controls (20) | 0–90 | 38 ± 10 | Negative |

*Irradiated CBA/Ca mice received aliquots of a 1:1.5 mixture of T6 cells transformed with herpes virus tk plasmid and ligated herpes virus tk gene and Ca cells mock-transformed with salmon sperm DNA. These mice are designated "primary." Recipients of marrow from primary animals are designated secondary and bear the same identifying number.
**Primary animal #3 was not treated with Mtx and was followed for 47 days.
N.T. = not tested.

As seen in Table IX, only the methotrexate-treated primary recipient animals showed a predominance of the T6 karyotype. An untreated animal and secondary recipients of marrow from primary recipients demonstrated predominance of the Ca karyotype. Similar results were seen in three other experiments in which animals were followed for 60 days. In one of these experiments Ca cells were transformed and T6 cells served as controls.

Herpes Simplex Virus Sequences In Mouse Hematopoietic Cells

To unambiguously demonstrate insertion of viral genes into proliferating marrow cells, DNA from spleens of experimental and control mice was extracted and subjected to Southern blot analysis. (Southern, J. Mol. Biol. 98: 503, 1975) DNA from these sources was cut with the restriction enzyme Eco/R1 and transferred to nitrocellulose strips after agarose gel electrophoresis. The strips were incubated with $P^{32}$-labeled herpes virus Bam H1 fragment containing DNA sequence coding for tk under hybridizing conditions and then analyzed by autoradiography. As shown in Table 2, herpes virus sequences were demonstrable in spleen DNA of primary recipient mice receiving bone marrow transformed in vitro and selected by drug pressure in vivo. Control mice and secondary recipient mice from the same experiment but lacking T6 predominance failed to demonstrate herpes tk sequences.

The transfer of genes for drug resistance to hematopoietic cells in vitro and their selection in intact animals in vivo provides for a variety of clinical applications. Such applications include the transfer of drug resistance genes with the objective of enabling patients with cancer to tolerate higher doses of anti-neoplastic drugs and insertion of genes which confer a proliferative advantage coupled to other genes to treat human genetic diseases such as the hemoglobinopathes.

In the past, supression of bone marrow hematopoiesis has been a major limitation to intensive treatment with most anticancer chemotherapeutic drugs. By enhancing resistance of marrow cells, higher dosages may be permitted in the treatment of cancers of other tissues. The above data have demonstrated that mice receiving marrow transformed with Mtx-resistant DNA tolerate high doses of Mtx for long periods of time with nearly normal hematologic parameters. With the hemoglobinopathies, insertion of a normally regulated and structurally normal $\beta$-globin gene should be capable of correcting the defect in $\beta$-thalassemia and sickle cell disease. By using the normally regulated and structurally normal $\beta$-globin gene in conjunction with a selective marker to allow for selective pressure in the host, the cells containing the selective marker and structurally normal $\beta$-globin gene should proliferate under the selective pressure of drug treatment.

The subject invention can be employed with host cells having a deficiency which results in a low rate of proliferation. By introduction of DNA providing for correction of the deficiency, the modified cells would have a proliferative advantage over unmodified cells of the same type. This situation may be illustrated by cases of combined immunodeficiency disease in which there is an adenosine deaminase deficiency.

The subject invention demonstrates that with appropriate selective conditions, naturally occurring or stress induced, modified cells under proliferating conditions can be given a selective advantage over the unmodified host cell. Thus, mammalian hosts can be provided with different or enhanced capabilities as a result of or concurrent with introduction of DNA providing for a selective advantage.

Although the foregoing invention has been described in some detail by way of illustration and example for purposes of clarity of understanding, it will be obvious that certain changes and modifications may be practiced within the scope of the appended claims.

What is claimed is:

1. A method for enhancing the genetic capability of a mammalian host by employing mammalian cells having exogenous genetic material capable of expression which comprises:
   isolating regenerative mammalian parent cells from a mammlian source compatible with said host;
   combining said regenerative mammalian parent cells with DNA including at least one gene capable of providing a selective advantage over the parent cell due to a naturally occurring deficiency or external stress inducement, said combining being under conditions where said DNA is introduced into said parent cell to produce modified cells; and
   introducing said modified cells into a compatible mammalian host under naturally occurring deficiency conditions or external stress induced conditions in said host providing said selective advantage, whereby said modified cells regenerate in said host at the source of said cells.

2. A method according to claim 1, wherein said parent cells are in the dividing phase.

3. A method according to claim 1, wherein said one gene providing a selective advantage expresses an enzyme.

4. A method according to any of claims 1, 2 or 3, wherein said parent cells are bone marrow stem cells.

5. A method according to claim 3, wherein said enzyme is inhibited by a chemotherapeutic drug and said external stress induced conditions in said host comprise administering to said host said chemotherapeutic drug.

6. A method according to claim 5, wherein said drug is methotrexate.

7. A method according to claim 1, including the additional step of isolating said modified cells from said host.

* * * * *